(12) United States Patent
Hofmann

(10) Patent No.: US 6,763,264 B2
(45) Date of Patent: Jul. 13, 2004

(54) METHOD OF TREATMENT USING ELECTROPORATION MEDIATED DELIVERY OF DRUGS AND GENES

(75) Inventor: Gunter A. Hofmann, San Diego, CA (US)

(73) Assignee: Genetronics, Inc., San Diego, CA (US)

( * ) Notice: Subject to any disclaimer, the term of this patent is extended or adjusted under 35 U.S.C. 154(b) by 0 days.

(21) Appl. No.: 10/213,514

(22) Filed: Aug. 6, 2002

(65) Prior Publication Data

US 2003/0097089 A1 May 22, 2003

Related U.S. Application Data

(63) Continuation of application No. 09/427,151, filed on Oct. 25, 1999, now Pat. No. 6,451,002, which is a continuation of application No. 08/537,265, filed on Sep. 29, 1995, now Pat. No. 5,993,434, which is a continuation-in-part of application No. 08/467,566, filed on Jun. 6, 1995, now Pat. No. 5,702,359, which is a continuation-in-part of application No. 08/042,039, filed on Apr. 1, 1993, now Pat. No. 5,439,440.

(51) Int. Cl.[7] .............................................. A61N 1/30
(52) U.S. Cl. ...................................................... 604/21
(58) Field of Search ............................ 604/501, 20–21; 435/173.6

(56) References Cited

U.S. PATENT DOCUMENTS

| | | | |
|---|---|---|---|
| 1,099,062 A | * | 6/1914 | Laposkey |
| 4,528,265 A | * | 7/1985 | Becker .......................... 604/20 |
| 4,784,737 A | * | 11/1988 | Ray et al. ....................... 604/21 |
| 4,955,378 A | | 9/1990 | Grasso |
| 5,019,034 A | | 5/1991 | Weaver et al. |
| 5,058,605 A | * | 10/1991 | Slovak |
| 5,128,257 A | | 7/1992 | Baer |
| 5,137,817 A | * | 8/1992 | Busta et al. |
| 5,273,525 A | * | 12/1993 | Hofmann |
| 5,389,069 A | * | 2/1995 | Weaver |
| 5,439,440 A | * | 8/1995 | Hofmann |
| 5,468,223 A | * | 11/1995 | Mir |
| 5,674,267 A | * | 10/1997 | Mir et al. |
| 5,702,359 A | * | 12/1997 | Hofmann et al. |
| 5,873,849 A | * | 2/1999 | Bernard |
| 5,993,434 A | * | 11/1999 | Dev et al. |
| 6,009,347 A | * | 12/1999 | Hofmann |
| 6,041,252 A | * | 3/2000 | Walker et al. |
| 6,110,161 A | * | 8/2000 | Mathiesen et al. |
| 6,261,281 B1 | * | 7/2001 | Mathiesen et al. |
| 6,278,895 B1 | * | 8/2001 | Bernard |

FOREIGN PATENT DOCUMENTS

| | | | | |
|---|---|---|---|---|
| WO | 8910690 | * | 11/1989 | ................. 604/20 |
| WO | 9422526 | * | 10/1994 | |

OTHER PUBLICATIONS

"The Effects of a Single High Voltage Electrical Stimulation with an Anticancer Drug on in vivo Growing Malignant Tumors" Japanese Journal of Surgery Vol 20 No 22 pp 197–204, 1990.*

* cited by examiner

*Primary Examiner*—Mark Bockelman
(74) *Attorney, Agent, or Firm*—Biotechnology Law Group

(57) ABSTRACT

A method for in vivo electrotherapy, or electroporation-mediated therapy, using a needle array apparatus is provided. Treatment of tumors with a combination of electroporation using the apparatus of the invention, and a chemotherapeutic agent, caused regression of tumors in vivo.

39 Claims, 16 Drawing Sheets

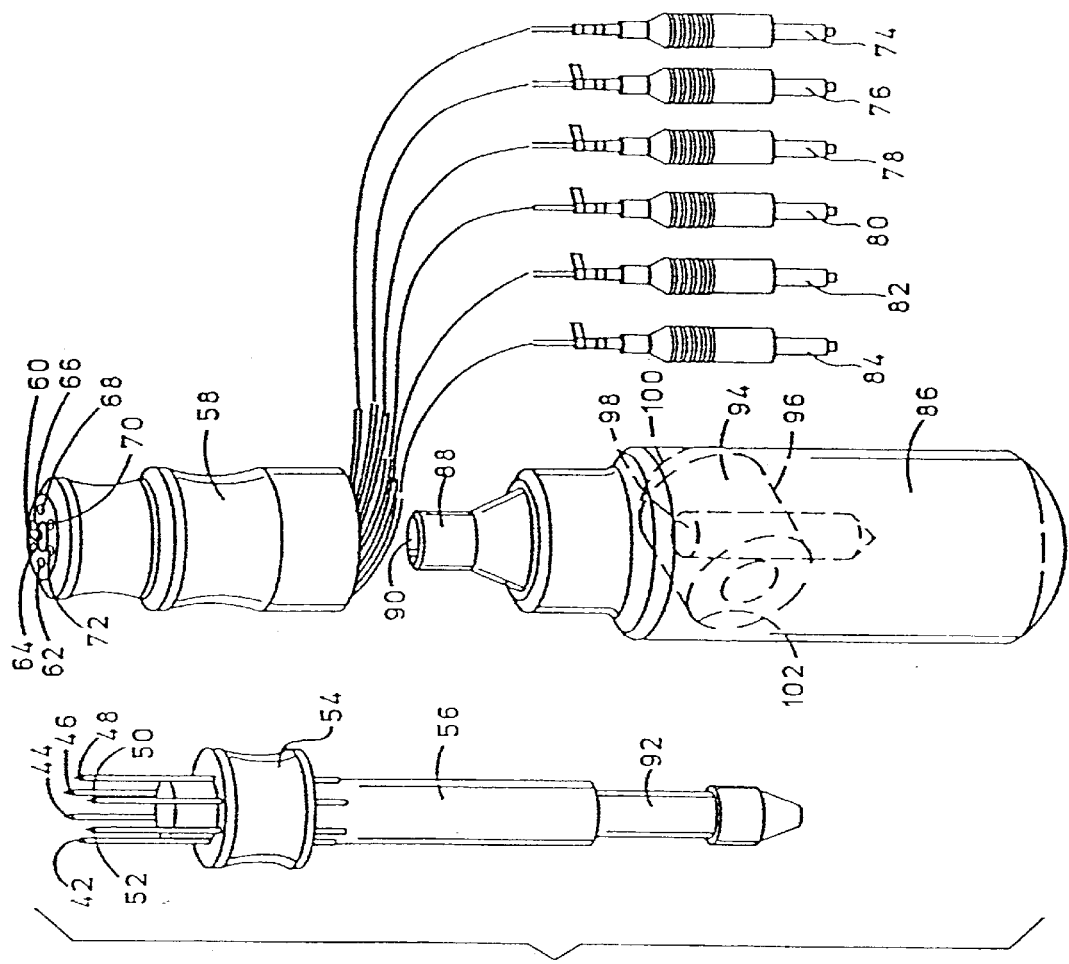
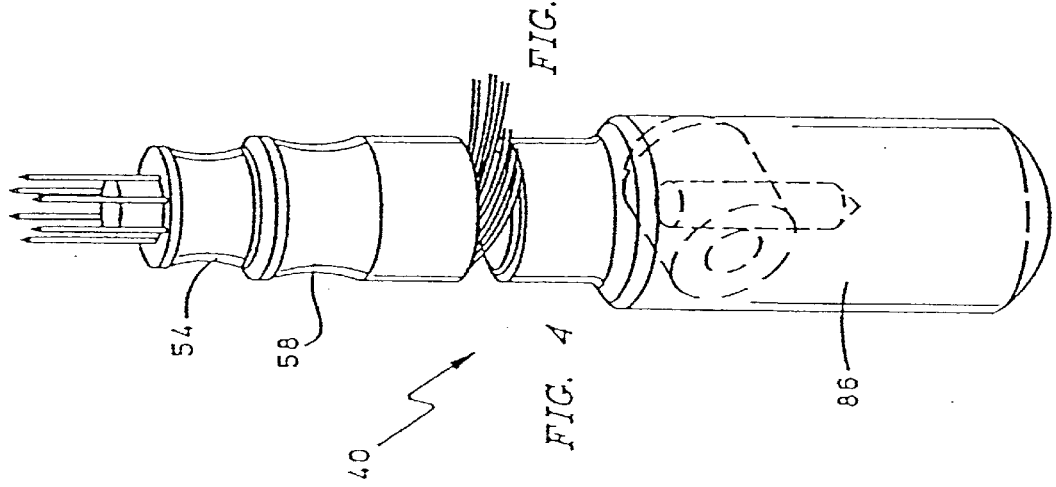

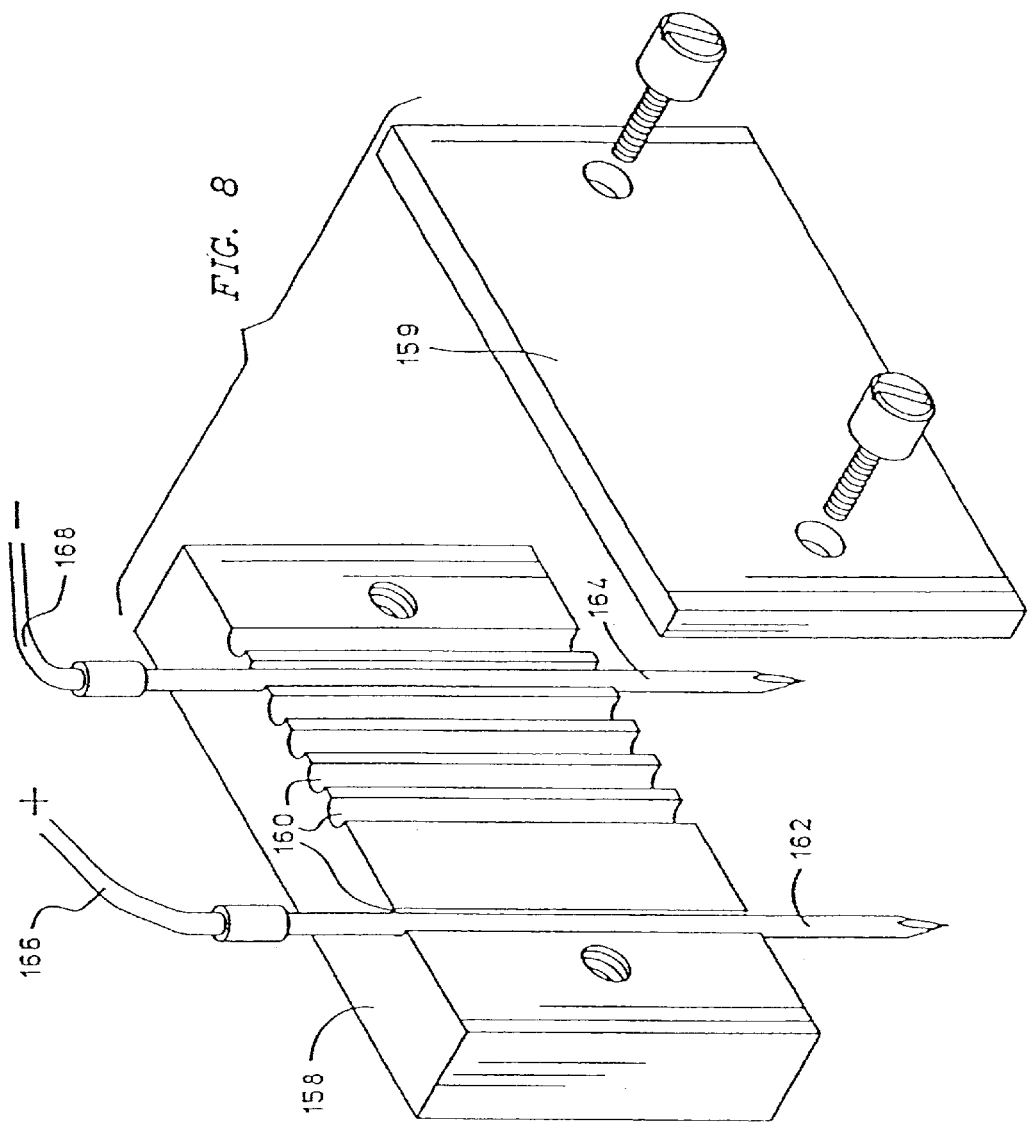

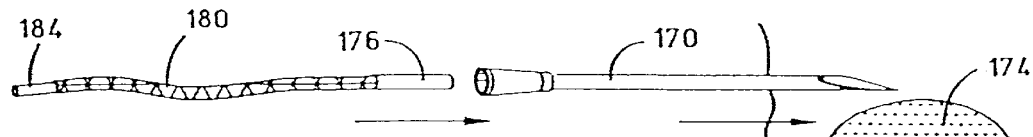
FIG. 9a
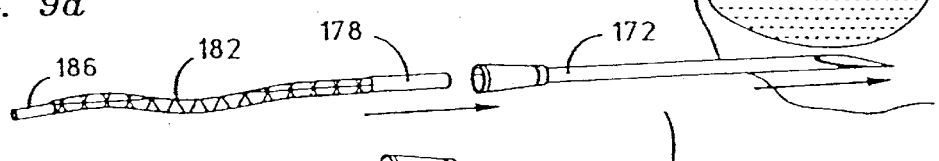
FIG. 9b
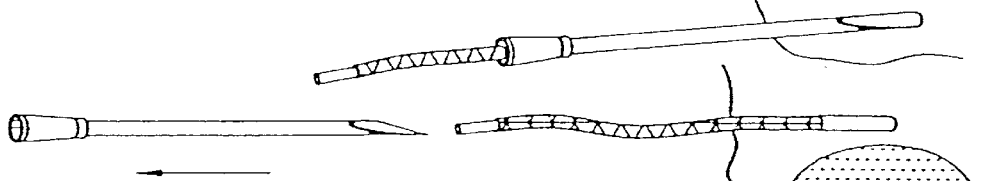
FIG. 9c
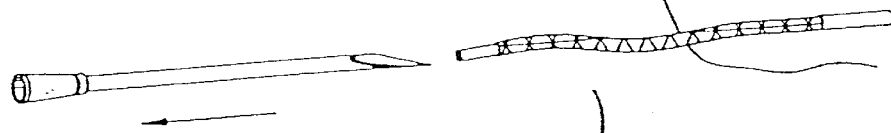
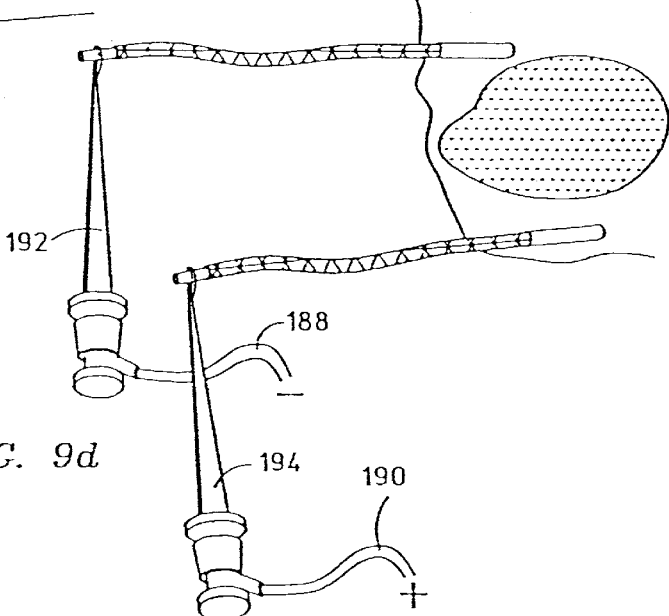
FIG. 9d

TUMOR GROWTH OF PANC3 AFTER ELECTROCHEMOTHERAPY WITH BLEOMYCIN
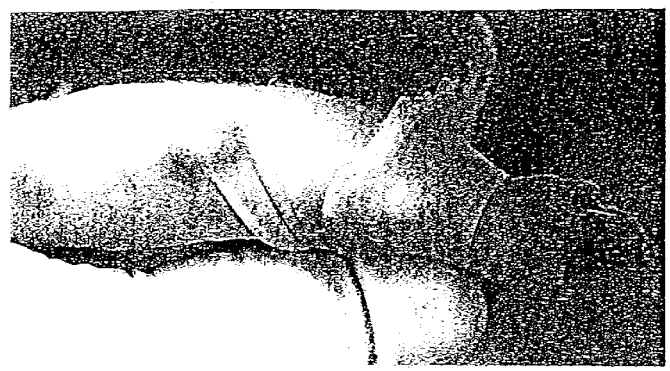
CONTROL (D+E−)
AFTER 29 DAYS
TREATED (D+E+)
AFTER 9 DAYS
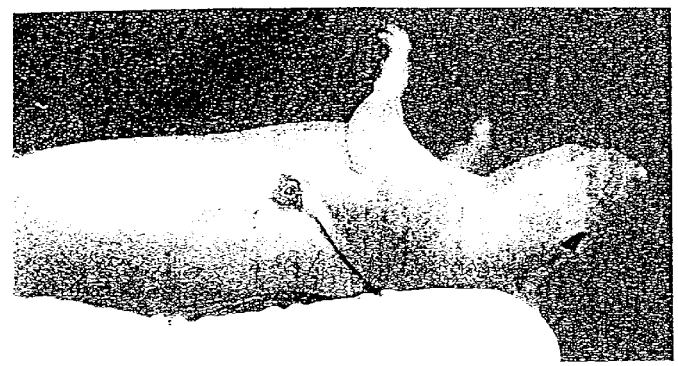
TREATED (D+E)
AFTER 29 DAYS
TREATED (D+E+)
AFTER 46 DAYS
*FIG. 11*

METHOD OF TREATMENT USING ELECTROPORATION MEDIATED DELIVERY OF DRUGS AND GENES

REFERENCE TO RELATED APPLICATIONS

The present application is a Continuation-in-Part of co-pending application Ser. No. 08/467,566, filed on Jun. 6, 1995, which is a Continuation-in-Part of co-pending application Ser. No. 08/042,039 filed on Apr. 1, 1993.

BACKGROUND OF THE INVENTION

The present invention relates to the treatment of ailments in humans and other mammals, and more particularly, to an improved method and apparatus for the application of controlled electric fields for in vivo delivery of genes and pharmaceutical compounds into live cells of a patient by electroporation.

In the 1970's it was discovered that electric fields could be used to create pores in cells without causing permanent damage to them. This discovery made possible the insertion of large molecules into cell cytoplasm. It is known that genes and other molecules such as pharmacological compounds can be incorporated into live cells through a process known as electroporation. The genes or other molecules are mixed with the live cells in a buffer medium and short pulses of high electric fields are applied. The cell membranes are transiently made porous and the genes or molecules enter the cells. There they can modify the genome of the cell.

Electroporation has been recently suggested as one approach to the treatment of certain diseases such as cancer. For example, in the treatment of certain types of cancer with chemotherapy it is necessary to use a high enough dose of a drug to kill the cancer cells without killing an unacceptable high number of normal cells. If the chemotherapy drug could be inserted directly inside the cancer cells, this objective could be achieved. Some of the best anti-cancer drugs, for trample, bleomycin, normally cannot penetrate the membranes of certain cancer cells. However, electroporation makes it possible to insert the bleomycin into the cells.

One therapeutic application of electroporation is for cancer treatment. Experiments on laboratory mammals have been carried out and reported as follows: Okino, M., E. Kensuke, 1990. *The Effects of a Single High Voltage Electrical Stimulation with an Anticancer Drug on in vivo Growing Malignant Tumors*. Jap. Journal of Surgery. 20:197–204. Mir, L. M., S. Orlowski, J. Belehradek Jr., and C. Paoletti. 1991. *Electrochemotherapy Potentiation of Antitumor Effect of Bleomycin by Local Electric Pulses*. Eur. J. Cancer. 27:68–72. Clinical trials have been conducted and reported by Mir, L. M., M. Belehradek, C. Domenge, S. Orlowski, B. Poddevin, et al. 1991. *Electrochemotherapy, a novel antitumor treatment: first clinical trial*. C.R. Acad. Sci. Paris. 313:613–618.

This treatment is carried out by infusing an anticancer drug directly into the tumor and applying an electric field to the tumor between a pair of electrodes. The field strength must be adjusted reasonably accurately so that electroporation of the cells of the tumor occurs without damage, or at least minimal damage, to any normal or healthy cells. This can normally be easily carried out with external tumors by applying the electrodes to opposite sides of the tumor so that the electric field is between the electrodes. The distance between the electrodes can then be measured and a suitable voltage according to the formula E=V/d can then be applied to the electrodes (E=electric field strength in V/cm; V=voltage in volts; and d=distance in cm). When internal tumors are to be treated, it is not easy to properly locate electrodes and measure the distance between them. In the aforementioned parent application, there is disclosed a system of electrodes for in vivo electroporation wherein the electrodes may be inserted into body cavities. In a related U.S. Pat. No. 5,273,25 a syringe for injecting molecules and macromolecules for electroporation utilizes needles for injection which also function as electrodes. This construction enables the subsurface placement of electrodes. It would be desirable to have an electrode apparatus having electrodes that can be inserted into or adjacent tumors so that predetermined electric fields can be generated in the tissue for electroporation of the cells of the tumor.

Studies have also shown that large size nucleotide sequences (up to 630 kb) can be introduced into mammalian cells via electroporation (Eanault, et al., *Gene (Amsterdam)*, 144(2):205, 1994; *Nucleic Acids Research*, 15(3):1311, 1987; Knutson, et al, *Anal. Biochem.*, 164:44, 1987; Gibson, et al., EMBO J., 6(8):2457, 1987; Dower, et al., *Genetic Engineering*, 12:275, 1990; Mozo, et al., *Plant Molecular Biology*, 16:917, 1991), thereby affording an efficient method of gene therapy, for example.

SUMMARY OF THE INVENTION

Accordingly, it is a primary object of the present invention to provide an improved apparatus that can be conveniently and effectively positioned to generate predetermined electric fields in pre-selected tissue.

It is another principal object of the present invention to provide an improved apparatus that provides an effective and convenient means for positioning electrodes into tissue for the injection of therapeutic compounds into the tissue and application of electric fields to the tissue.

In accordance with a primary aspect of the present invention an electrode apparatus for the application of electroporation to a portion of the body of a patient, comprises a support member, a plurality of needle electrodes adjustably mounted on said support member for insertion into tissue at selected positions and distances from one another, and means including a signal generator responsive to said distance signal for applying an electric signal to the electrodes proportionate to the distance between said electrodes for generating an electric field of a predetermined strength.

Another aspect of the invention includes needles that function for injection of therapeutic substances into tissue and function as electrodes for generating electric fields for portion of cells of the tissue.

In yet another aspect of the invention is provided a therapeutic method utilizing the needle array apparatus for the treatment of cells, particularly tumor cells.

BRIEF DESCRIPTION OF THE DRAWINGS

FIG. 3 is an assembly drawing showing a perspective view of an alternate embodiment of the invention.

FIG. 4 is a perspective view of the embodiment of FIG. 3 shown assembled.

FIG. 8 is a perspective view of a still further embodiment of the invention.

FIGS. 9a–9d is a top plan view, illustrating a preferred form of electrodes and sequence of use.

FIG. 11 is an illustration of tumor growth of Panc-3 cells after ECT with bleomycin in nude mice.

DETAILED DESCRIPTION OF THE PREFERRED EMBODIMENTS

As used herein the term "molecules" includes pharmacological agents, genes, antibodies or other proteins. One human therapeutic application of electroporation consists of infusion of an anticancer drug and electroporation of the drug into the tumor by applying voltage pulses between electrodes disposed on opposite sides of the tumor, called electrochemotherapy (ECT). The present invention was devised primarily for enabling ECT such as that reported by Okino and Mir et al to be carried out on non-surface tumors such as those inside the body. However, it may be utilized for other therapeutic applications.

Figures 1, 2:
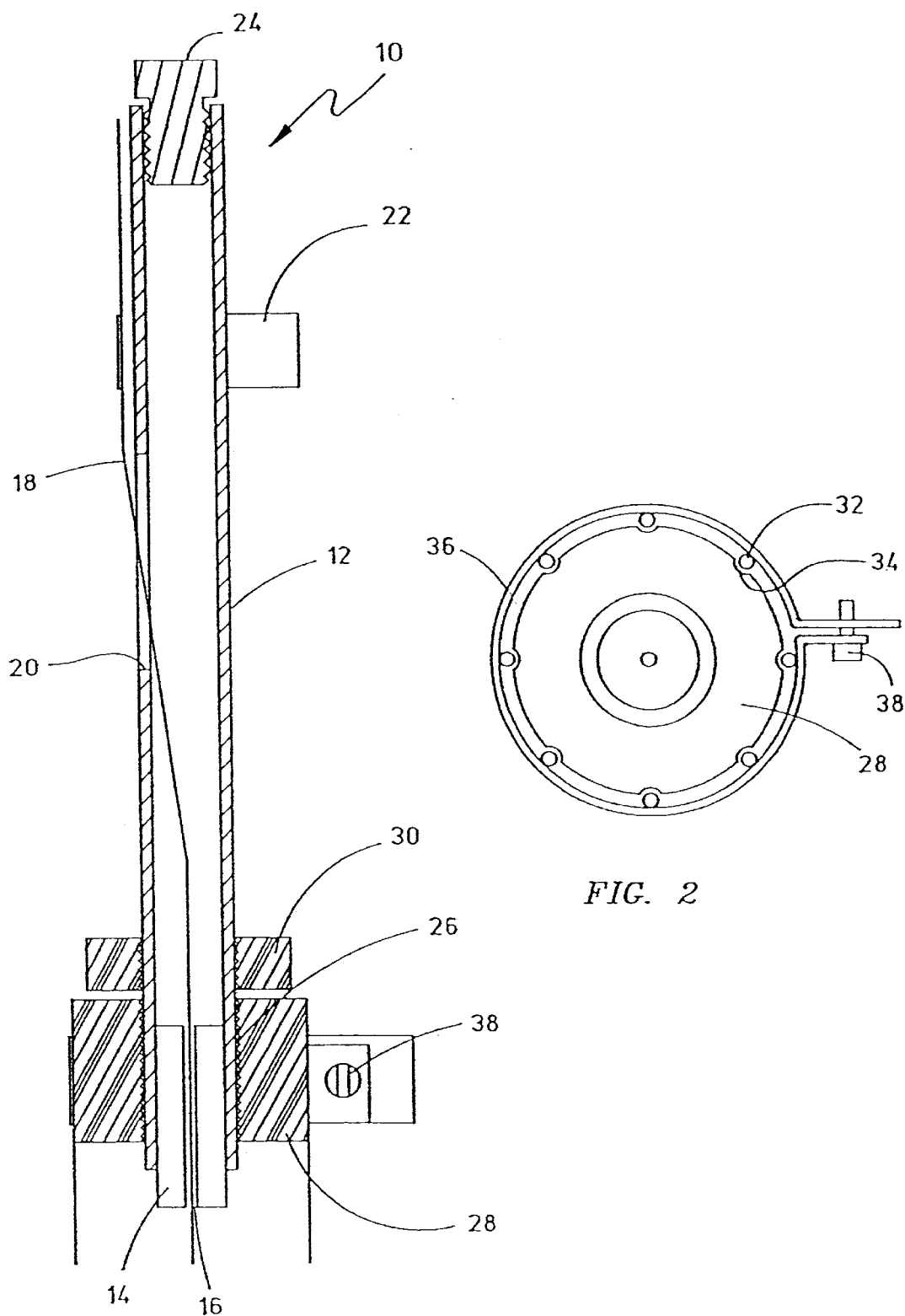
FIG. 1 is a side elevation view, in section of a needle assembly in accordance with a preferred embodiment of the invention.
FIG. 2 is a bottom view of the embodiment of FIG. 1.

Referring to FIG. 1 of the drawings, a needle assembly in accordance with preferred embodiment of the invention is illustrated and designated generally by the numeral 10. The needle assembly comprises an elongated tubular support body 12 which is preferably in the form of a hollow stainless steel shaft. A center needle mount 14 is mounted on the lower end of the shaft 12 and has a central bore 16 for receiving and guiding a center needle 18. The shaft 12 includes a needle exit slot 20 through which the needle electrode 18 extends from the interior thereof to the exterior where it is secured by a clamp 22 to the outside of the tube 12.

The upper end of the electrode 18 may be secured to a screw 24 for connection to an electrical circuit. The lower end of the tubular holder 12 includes threats 26 for threatably receiving a collar 28 for mounting a plurality of needles and a stop collar 30 for stopping or locking the collar 28 in position.

A plurality of needles 32 are mounted in grooves 34 equally spaced around the outer surface of the needle collar 28. This provides a circular array of equally spaced needles, eight in number in the illustrated embodiment. The needles are held in place by a band clamp 36, having the ends clamped together by a screw or nut and bolt 38 which also serves as an electrical connection for the needles. The band clamp 36 directly engages and holds the needles in place.

This electrode assembly is designed to apply electrical energy to living tissue when the needles are inserted into the tissue. The center needle 18 acts as one electrode, such as an anode or cathode, and the other or annular arrangement of needles 32 functions as the opposite electrode. All of these needles are held in fixed positions when the clamps are installed and secured. One or more of the needles may be cannular or tubular in form for injecting molecules of genes, pharmaceutical or other substances into the tissue.

In operation the center needle should be adjusted in order to achieve the desired tissue penetration. This is done by releasing the pressure of the center needle clamp 22 and sliding the center needle 18 outwardly or inwardly, as seen in FIG. 1, so that it extends from the center needle guide 14 to desired penetration distance. The needle is then clamped in position. Thereafter annular needles 32 are adjusted to achieve the desired penetration into the tissue. This can be accomplished by releasing the pressure of the band clamp 36 and sliding the needles 32 into the desired position. Minor adjustments can also be made by moving the needle collar 28 toward and away from the end of the shaft 12. A therapeutic substance may be injected into the tissue through one or more of these needles or by a separate means.

After all needles are adjusted to the proper penetration, the shaft 12 is grasped and the needles are inserted into the tissue to the desired depth. Thereafter, a suitable pulse generator is connected to the electrode assembly and the appropriate voltage applied to the electrodes. A suitable quantity of therapeutic substance such as genes or molecules of a suitable chemical or pharmaceutical for treatment of the tissue is injected into the tissue before the voltage is applied.

A modification to this electrode assembly could include a solid non-penetrating electrode (not shown) in place of the center needle. The non-penetrating center electrode could be any suitable shape conductor such as a button or plate attached to the end of the shaft 12 to contact the surface tissue. The annular needle arrangement would be adjusted to penetrate the tissue at the desired depth when the center electrode is resting on a tissue surface. Electrical energy would flow from the penetrating needles through the tissue and to the central electrode on the surface. These arrangements can be utilized to treat near surface tumors where the circular array of electrodes are designed to encircle the tumor. The central electrode is positioned such that the electrical energy flows through the tumor to the central electrode.

Other advantages of this electrode assembly are that all needles 18 and 32 can be independently adjusted to achieve the desired penetration. The needle 28 collar can also be adjusted to position it from the end of the shaft 12 so that insertion of the center and annular needles can be directly observed. In addition, the needle collar 28 can have any size or configuration to encircle the tissue area to be treated.

Referring to FIGS. 3 and 4 an alternate embodiment of a circular array needle electrode assembly is illustrated and designated generally by the numeral 40. This needle assembly comprises a circular array of needles 42 through 52, which are mounted in equally spaced relation in a hub 54 mounted on an elongated cylindrical shaft 56. The hub 54 is preferably of a suitably selected diameter to provide the desired diameter of the arrays to position around a tumor or other tissue to be treated. One or more of the needles may be hollow to enable the injection of molecules of a therapeutic substance, as will be more fully described hereinafter.

An electrical connector socket assembly comprises a body member 58 having a central opening or bore 60 for receipt of shaft 56 and, an annular array of a plurality of sockets 62 through 72 for receipt of the ends of needles 42 through 52. The sockets 62 through 72 electrically connect the needles to leads 74 through 84 which connect to a distributing switch, as will be subsequently described.

The electrical connector socket 58 fits onto shaft 56 with the end of the needles extending into the electrical sockets 62 through 72 for connecting to the leads 74 through 84. The shaft 56 which mounts the needle array hub 54 and the socket assembly 58 mounts onto a holder 86 adapted to be held in the hand. The holder 86 has an elongated cylindrical configuration adapted to be held in the hand for manipulation. The holder 86 has a forward socket and including a forwardly extending tubular shaft 88 having a bore 90 into which shaft 56 extends while the shaft 88 extends into a bore (not shown) within the connector member 58. The shaft 56 extends into bore 90 and has a annular groove or recess 92 which is engaged by a retainer latch which comprises a transverse plug 94 in a bore 96 biased to one side and including a bore 98 in which the annular slot 92 extends and is retained in the holder. A spring 102 mounted in bore 96 biases plug 94 to the latched position. The shaft 56 may be released for removal by pressing on end 100 of plug 94.

Figure 5:
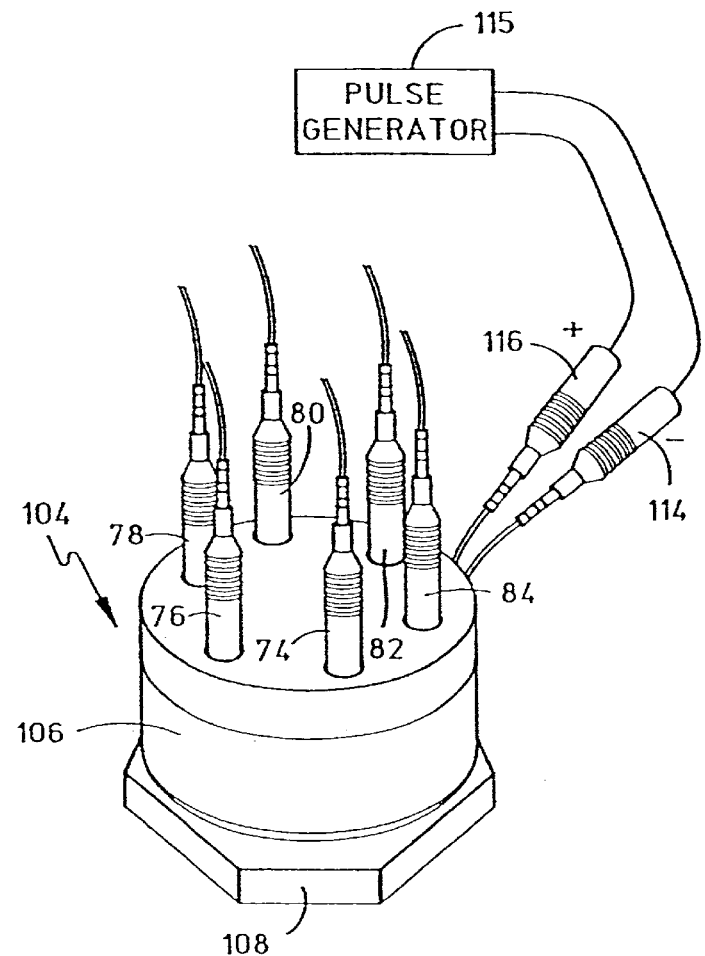
FIG. 5 is a perspective view of a selector switch for the electrode assembly of FIG. 4.
Figure 6C:
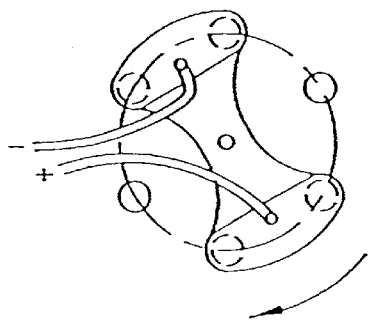

The holder when assembled as shown in FIG. 4 may be grasped in the hand and the needles inserted into a selected tissue area. The needles 42–52 are preferably spaced and positioned to surround the selected tissue of treatment. One or more of the needles 42–52, as previously explained, may be hollow to enable the injection of the desired therapeutic substance. The electrode leads 74–84 are then connected in a preferred arrangement to a rotatable switch assembly, as shown in FIG. 5, which enables the selection of opposed pairs of the needles for activation or the application of the electrical potential.

The switch assembly designated generally by the numeral 104 comprises a stationary housing 106 which, in the illustrated embodiment, is generally cylindrical in configuration and in which is mounted a rotor 108 with spaced contacts 110 and 112 connected by a pair of conductors 114 and 116 to a pulse power generator 115. The rotor contacts 110 and 112 are positioned within housing 106 to engage annular contacts 118, 120, 122, 124, 126 and 128 to which leads 74–84 are connected.

Figure 6A:
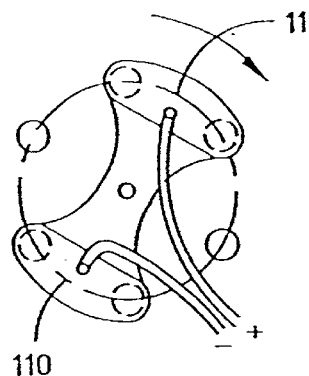
FIGS. 6a–6c is a diagrammatic illustration of selected contact positions of the switch of FIG. 5.
Figure 6B:
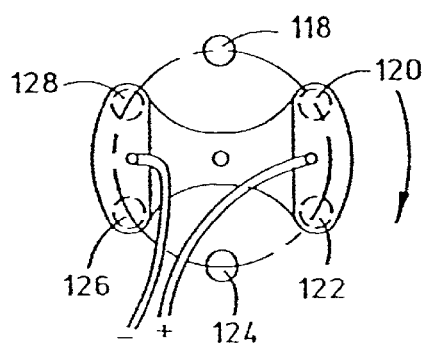

Referring to FIGS. 6a, b and c, the rotor 108 has an internal portion having contacts 110 and 112 each of which bridge between two contacts 118–128 to which the leads 74 through 84 are connected to connect the source of power. The internal contacts 110 and 112 rotate with the rotor 108 and can be selectively positioned in conductive relation with pairs of the internal contacts 118–128 to thereby activate opposed pairs of the needle electrodes. This enables the operator to selectively position the electrodes surrounding a selected tissue and to selectively apply the direction of the electrical field as desired for optimum treatment. The rotor 108 enables the field to be selectively generated around or across the tissue from all directions.

Figure 7:
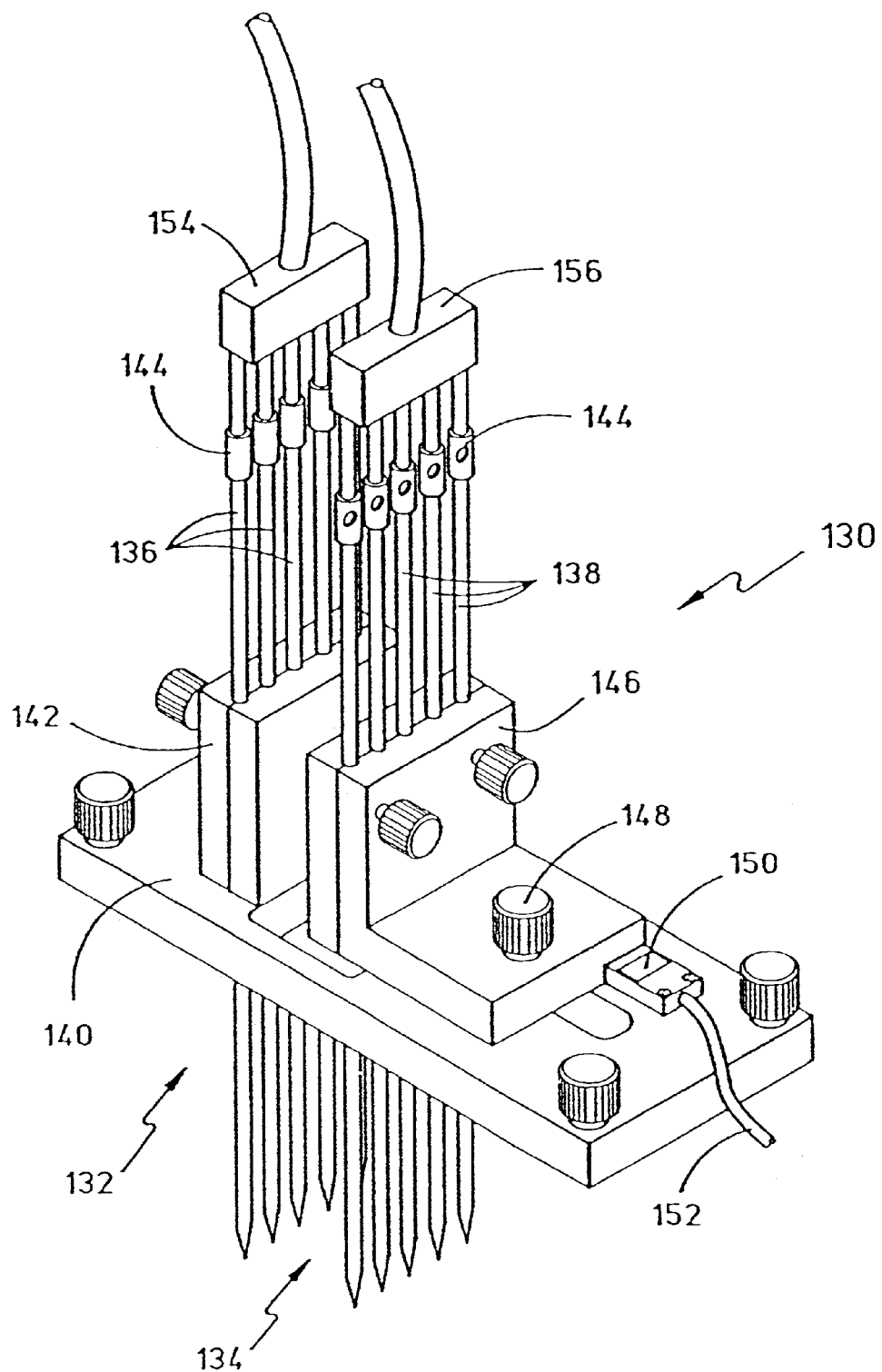
FIG. 7 is a perspective view of a further embodiment of the invention.

Referring to FIG. 7 an alternate embodiment of an electric field generating array of parallel adjustably positionable electrodes, as disclosed in the parent application, is illustrated. The electrode assembly designated generally by the numeral 130 includes a pair of spaced apart arrays 132 and 134 of conductive needle electrodes 136 and 138 mounted on a dielectric carrier or support member 140. The needle array 132 is held in a fixed clamp 142 which allows the needles 136 to be adjusted in depth relative to the support 140.

The needles 138 are mounted in a moveable clamp 146 which is adjustably mounted on support member 140 by a clamp screw 148. The needles 136 and 138 are each provided with a penetration stop 144. The gap spacing clamp screw 148 secures the clamp 146 in selected positions on the support 140. A gap spacing sensor 150 senses the distance between the needle arrays 132 and 134 and generates a signal that is sent to the pulse generator via conductor cable 152. A pulse generator is connected to the needle electrodes by means of cables 154 and 156.

Referring to FIG. 8, details of a needle holder or template for various arrangements for establishing a spaced pair or parallel arrays of needles is illustrated. This embodiment comprises a base holder member 158 having a plurality of adjacently positioned parallel slots 160 into which selected needles 162 and 164 may be positioned in selected spaced relation. This holder may serve to mount a pair of oppositely polarized needle electrodes 162 and 164, as illustrated. These can be selectively positioned in selected space relationship to be disposed on opposite sides of a selected tissue. The needles are clamped into the slots by a clamp or plate 159. In addition, the holder may be used in combination with an additional holder for provision of multiple arrays on opposite sides of a selected tissue. The illustrated needles may be connected by conductors 166 and 168 to a suitable pulse generator.

Referring to FIGS. 9a through 9d, an additional aspect of the invention is illustrated. As more clearly illustrated, the combination electrodes may take the form of separate needles 170 and 172 which may be first inserted into or beside a selected tissue area such as on opposite sides of a tumor 194 as illustrated. Thereafter the needles may be connected to a syringe or other source of molecules and used to inject a selected molecular solution into the tissue area. The needles may be non-conductive and a pair of electrodes 176 and 178, as illustrated in FIG. 9b, are selectively fed through the bore or lumen of the respective needles into the tissue, as illustrated, and thereafter the needle is removed, as shown in FIG. 9c. The electrodes 176 and 178 are each provided with an elongated insulated conductor 180 and 182 with conductive tips 184 and 186.

A pair of conductors 188 and 190 from a suitable power generator may then be connected to the ends of the conductors of the electrodes by micro clamps 192 and 194, as shown in 9d, and an electric potential applied across the electrodes. This generates a field in the tissue and electroporates the cells of the selected tissue, such as a tumor or the like. This electroporation enables the selected molecules to enter the cells of the tissue and more efficiently kill or alter the cells as desired. This form of needle and electrode may be used with any or all the above described assemblies.

These needle electrode assemblies, as above described, enable the in vivo positioning of electrodes in or adjacent to subsurface tumors or other tissue. While the focus of the present application has been on electrochemotherapy, the embodiment of the subject invention may be applied to other treatments, such as gene therapy of certain organs of the body.

The nature of the electric field to be generated is determined by the nature of the tissue, the size of the selected tissue and its location. It is desirable that the field be as homogenous as possible and of the correct amplitude. Excessive field strength results in lysing of cells, whereas a low field strength results in reduced efficacy. The electrodes may be mounted and manipulated in many ways including but not limited to those in the parent application. The electrodes may be conveniently manipulated on and by forceps to internal position.

The waveform of the electrical signal provided by the pulse generator can be an exponentially decaying pulse, a square pulse, a unipolar oscillating pulse train or a bipolar oscillating pulse train. The electric field strength can be 0.2 kV/cm to 20 kV/cm. The pulse length can be ten $\mu$s to 100 ms. There can be one to one hundred pulses. Of course, the waveform, electric field strength and pulse duration are also dependent upon the type of cells and the type of molecules that are to enter the cells via electroporation.

The various parameters including electric field strengths required for the electroporation of any known cell is generally available from the many research papers reporting on the subject, as well as from a database maintained by Genetronics, Inc., San Diego, Calif., assignee of the subject application. The electric fields needed for in vivo cell electroporation, such as ECT, are similar in amplitude to the fields required for cells in vitro. These are in the range of from 100 V/cm to several kV/cm. This has been verified by the inventors own experiments and those of others reported in scientific publications. The first in vivo application of pulsed electric fields in the chemotherapy field to treat tumors was reported in 1987 by Okino in Japan.

Pulse generators for carrying out the procedures described herein are and have been available on the market for a number of years. One suitable signal generator is the ELECTRO CELL MANIPULATOR Model ECM 600 commercially available from GENETRONICS, INC. of San Diego, Calif., U.S.A. The ECM 600 signal generator generates a pulse from the complete discharge of a capacitor which results in an exponentially decaying waveform. The electric signal generated by this signal generator is characterized by a fast rise time and an exponential tail. In the signal generator, the electroporation pulse length is set by selecting one of ten timing resistors marked R1 through R10. They are active in both High Voltage Mode (HVM) (capacitance fixed at fifty microfarads) and Low Voltage Mode (LVM) (with a capacitance range from 25 to 3,175 microfarads).

The ECM 600 signal generator has a control knob that permits the adjustment of the amplitude of the set charging voltage applied to the internal capacitors from 50 to 500 volts in LVM and from 0.05 to 2.5 kV in the HVM. The amplitude of the electrical signal is shown on a display incorporated into the ECM 600 signal generator. This device further includes a plurality of push button switches for controlling pulse length, in the Low VM mode, by a simultaneous combination of resistors parallel to the output and a bank of seven selectable additive capacitors.

The ECM 600 signal generator also includes a single automatic charge and pulse push button. This button may be depressed to initiate both charging of the internal capacitors to the set voltage and to deliver a pulse to the outside electrodes in an automatic cycle that takes less than five seconds. The manual button may be sequentially pressed to repeatedly apply the predetermined electric field.

Preferably, the therapeutic method of the invention utilizes a square wave pulse electroporation system. For example, the ElectroSquarePorator (T820), also available from GENETRONICS, INC., can be used.

Square wave electroporation systems deliver controlled electric pulses that rise quickly to a set voltage, stay at that level for a set length of time (pulse length), and then quickly drop to zero. This type of system yields better transformation efficiency for the electroporation of plant protoplast and mammalian cell lines than an exponential decay system.

The ElectroSquarePorator (T820) is the first commercially available square wave electropomtion system capable of generating up to 3000 volts. The pulse length can be adjusted from 5 $\mu$sec to 99 msec. The square wave electroporation pulses have a gentler effect on the cells which results in higher cell viability.

The T820 ElectroSquarePorator is active in both the High Voltage Mode (HVM) (100–3000 volts) and the Low Voltage Mode (LVM) (50–500 volts). The pulse length for LVM is about 0.3 to 99 msec and for HVM, 5 to 99 $\mu$sec. The T820 has multiple pulsing capability from about 1 to 99 pulses.

Mir and others have used square wave pulses for electrochemotherapy, which allows the insertion of chemotherapeutic agents into cancerous tumors. Mice were injected with a low dose of bleomycin. The cancerous tumors were then electroporated resulting in the reduction or complete remission of the tumors (Mir, L. M., *Eur. J. Cancer*, 27(1):68, 1991).

Saunders has compared the square wave with exponential decay pulses in the electroporation of plant protoplast. Square wave electroporation produced higher transformation efficiency than the exponential decay pulses. He also reported that the optimization of electroporation parameters is much easier with square wave pulses since sufficient transformation efficiency can be produced over a larger range of voltages (Saunders, *Guide to Electroporation and Electrofusion*, pp. 227–247, 1991).

The therapeutic method of the invention includes electrotherapy, also referred to herein as electroporation-mediated therapy, using the apparatus of the invention for the delivery of macromolecules to a cell or tissue. As described earlier, the term "macromolecule" or "molecule" as used herein refers to drugs (e.g., chemotherapeutic agents), nucleic acids (e.g., polynucleotides), peptides and polypeptides, including antibodies. The term polynucleotides include DNA, cDNA and RNA sequences.

Drugs contemplated for use in the method of the invention are typically chemotherapeutic agents having an antitumor or cytotoxic effect. Such drugs or agents include bleomycin, neocarcinostatin, suramin, and cisplatin. Other chemotherapeutic agents will be known to those of skill in the art (see for example The Merck Index). The chemical composition of the agent will dictate the most appropriate time to administer the agent in relation to the administration of the electric pulse. For example, while not wanting to be bound by a particular theory, it is believed that a drug having a low isoelectric point (e.g., neocarcinostatin, IEP=3.78), would likely be more effective if administered post-electroporation in order to avoid electrostatic interaction of the highly charged drug within the field. Further, such drugs as bleomycin, which have a very negative log P, (P being the partition coefficient between octanol and water), are very large in size (MW=1400), and are hydrophilic, thereby associating closely with the lipid membrane, diffuse very slowly into a tumor cell and are typically administered prior to or substantially simultaneous with the electric pulse. Electroporation facilitates entry of bleomycin or other similar drugs into the tumor cell by creating pores in the cell membrane.

It may be desirable to modulate the expression of a gene in a cell by the introduction of a molecule by the method of the invention. The term "modulate" envisions the suppression of expression of a gene when it is over-expressed, or augmentation of expression when it is underexpressed. Where a cell proliferative disorder is associated with the expression of a gene, nucleic acid sequences that interfere with the gene's expression at the translational level can be used. This approach utilizes, for example, antisense nucleic acid, ribozymes, or triplex agents to block transcription or translation of a specific mRNA, either by masking that mRNA with an antisense nucleic acid or triplex agent, or by cleaving it with a ribozyme.

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target cell. The use of antisense methods to inhiiit the in vitro translation of genes is well known in the art (Marcus-Sakura, *Anal. Biochem.*, 172: 289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.*, 1(3):227, 1991; Helene, C., *Anticancer Drug Design*, 6(6):569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The present invention also provides gene therapy for the treatment of cell proliferative or immunologic disorders mediated by a particular gene or absence thereof. Such therapy would achieve its therapeutic effect by introduction of a specific sense or antisense polynucleotide into cells having the disorder. Delivery of polynucleotides can be achieved using a recombinant expression vector such as a chimeric virus, or the polynucleotide can be delivered as "naked" DNA for example.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). When the subject is a human, a vector such as the gibbon ape leukemia virus (GaLV) can be utilized. A number of additional retroviral vectors can incorporate multiple genes. All of these vectors can transfer or incorporate a gene for a selectable marker so that transduced cells can be identified and generated.

Therapeutic peptides or polypeptides may also be included in the therapeutic method of the invention. For example, immunomodulatory agents and other biological response modifiers can be administered for incorporation by a cell. The term "biological response modifiers" is meant to encompass substances which are involved in modifying the immune response. Examples of immune response modifiers include such compounds as lymphokines. Lymphokines include tumor necrosis factor, interleukins 1, 2, and 3, lymphotoxin, macrophage activating factor, migration inhibition factor, colony stimulating factor, and alpha-interferon, beta-interferon, and gamma-interferon and their subtypes.

Also included are polynucleotides which encode metabolic enzymes and proteins, including antiangiogenesis compounds, e.g., Factor VIII or Factor IX.

The macromolecule of the invention also includes antibody molecules. The term "antibody" as used herein is meant to include intact molecules as well as fragments thereof, such as Fab and F(ab')$_2$.

Administration of a drug, polynucleotide or polypeptide, in the method of the invention can be, for example, parenterally by injection, rapid infusion, nasopharyngeal absorption, dermal absorption, and orally. In the case of a tumor, for example, a chemotherapeutic or other agent can be administered locally, systemically or directly injected into the tumor. When a drug, for example, is administered directly into the tumor, it is advantageous to inject the drug in a "fanning" manner. The term "fanning" refers to administering the drug by changing the direction of the needle as the drug is being injected or by multiple injections in multiple directions like opening up of a hand fan, rather than as a bolus, in order to provide a greater distribution of drug throughout the tumor. As compared with a volume that is typically used in the art, it is desirable to increase the volume of the drug-containing solution, when the drug is administered (e.g., injected) intratumorally, in order to insure adequate distribution of the drug throughout the tumor. For example, in the EXAMPLES herein, one of skill in the art typically injects 50 $\mu$l of drug-containing solution, however, the results are greatly improved by increasing the volume to 150 $\mu$l. Preferably, the injection should be done very slowly and at the periphery rather than at the center of the tumor where the intertitial pressure is very high.

Preferably, the molecule is administered substantially contemporaneously with the electroporation treatment. The term "substantially contemporaneously" means that the molecule and the electroporation treatment are administered reasonably close together with respect to time. The administration of the molecule or therapeutic agent can at any interval, depending upon such factors, for example, as the nature of the tumor, the condition of the patient, the size and chemical characteristics of the molecule and half-life of the molecule.

Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable forms for suspending the liposomes include emulsions, suspensions, solutions, syrups, and elixirs containing inert diluents commonly used in the art, such as purified water. Besides the inert diluents, such compositions can also include adjuvants, wetting agents, emulsifying and suspending agents. Further, vasoconstrictor agents can be used to keep the therapeutic agent localized prior to pulsing.

Any cell can be treated by the method of the invention. The illustrative examples provided herein demonstrate the use of the method of the invention for the treatment of tumor cells, e.g., pancreas and lung. Other cell proliferative disorders are amenable to treatment by the electroporation method of the invention. The term "cell proliferative disorder" denotes malignant as well as non-malignant cell populations which often appear to differ from the surrounding tissue both morphologically and genotypically. Malignant cells (i.e., tumors or cancer) develop as a result of a multi-step process. The method of the invention is useful in treating malignancies or other disorders of the various organ systems, particularly, for example, cells in the pancreas and lung, and also including cells of heart, kidney, muscle, breast, colon, prostate, thymus, testis, and ovary. Preferably the subject is human.

The following examples are intended to illustrate but not limit the invention. While they are typical of those that might be used, other procedures known to those skilled in the art may alternatively be used.

EXAMPLES

The following examples illustrate the use of electro-chemotherapy (ECT) of a poorly differentiated human pancreatic tumor (Panc-3) xenografted subcutaneously on the left flank of nude mice. The single treatment procedure involved injection of bleomycin (0.5 units in 0.15 ml saline) intratumorally, using farming, as described herein followed by application of six square wave electrical pulses, ten minutes later, using proprietary needle array electrodes arranged along the circumference of a circle 1 cm in diameter. Needle array of variable diameters (e.g., 0.5 cm, 0.75 cm and 1.5 cm can also be used to accommodate tumors of various sizes. Stoppers of various heights can be inserted at the center of the array to make the penetration depth of the needles into the tumor variable. A built-in mechanism allowed switching of electrodes for maximum coverage of the tumor by the pulsed field. The electrical parameters were: 1300 V/cm and 6×99 µs pulses spaced at 1 sec interval.

Results showed severe necrosis and edema in nearly all the mice at the treatment site. While there was a substantial reduction in the tumor volume (after a slight initial increase due to edema) of the mice in the treated group (D+E+; D=Drug, E=Electrical field), those in the control group (D+E−) increased dramatically. Nearly complete tumor regression was observed in 90% of the mice treated by ECT after 28 days. No response was seen in 10% of the mice. A complete regression with no palpable tumor has been observed in 60% of the cases 77 days after the initial treatment. However, there was tumor regrowth in 20% of the mice 35 days after treatment but at a much slower growth rate compared to the control. This observation has been linked to incomplete treatment of large primary tumors where the needle depth was lower than the Z dimension of the tumor. Histological analysis of tumor samples showed necrotic tumor cell ghosts in D+E+ group compared to a mixture of viable and necrotic cells in D+E− group. Preliminary studies with human non-small cell lung cancer (NSCLC) tumors xenografted onto nude mice have also shown very encouraging results with ECT treatment with bleomycin.

Example 1

The tumor cell line Pant-3, a poorly differentiated adenocarcinoma cell line of the pancreas, was supplied by Anticancer, Inc., San Diego. For ECT experiments, tissue taken from the stock mice, where the tumor line was maintained, was thawed and cut into very small pieces about 1 mm each, and 8–10 pieces were surgically xenografted in a subcutaneous sac made in left flank of nude mice, and then closed with 6.0 surgical suture. After the average tumor size reached about 5 mm, mice with palpable tumors were divided randomly, 10 mice for control group (D+E−; D=Drug, E=Electric field) and 10 mice for ECT treatment, namely bleomycin injection followed by pulsing (D+E+) from a BTX Square Wave T820 Generator. The tumor dimensions were measured and the tumor volume calculated using the formula:

$$(\Pi/6) \times a \times b \times c$$

where a, b, and c are, respectively, the length, width and thickness of the tumor. 0.5 units Bleomycin (Sigma Chemicals) was dissolved in 0.15 ml of 0.9% NaCl and was injected in each mice intratumorally by fanning for both the control (D+E−) and the treated (D+E+) groups. Ten minutes after the injection, each mouse in the D+E+ group was pulsed from a BTX T820 square wave electroporator with a set of needle array electrodes as described in the present invention. Electrical parameters used were as follows: field strength 1300 V/cm, 6 pulses of 99 µs each, at 1 sec interval.

The mice were monitored every day for mortality and any signs of a diseased state were noted. The tumor dimensions were measured at regular intervals and tumor growth regression/progression monitored. Another set of nude mice with xenografts of non-small cell lung cancer line was also treated by the same procedure as for the Panc-3 tumors.

Figure 10A:
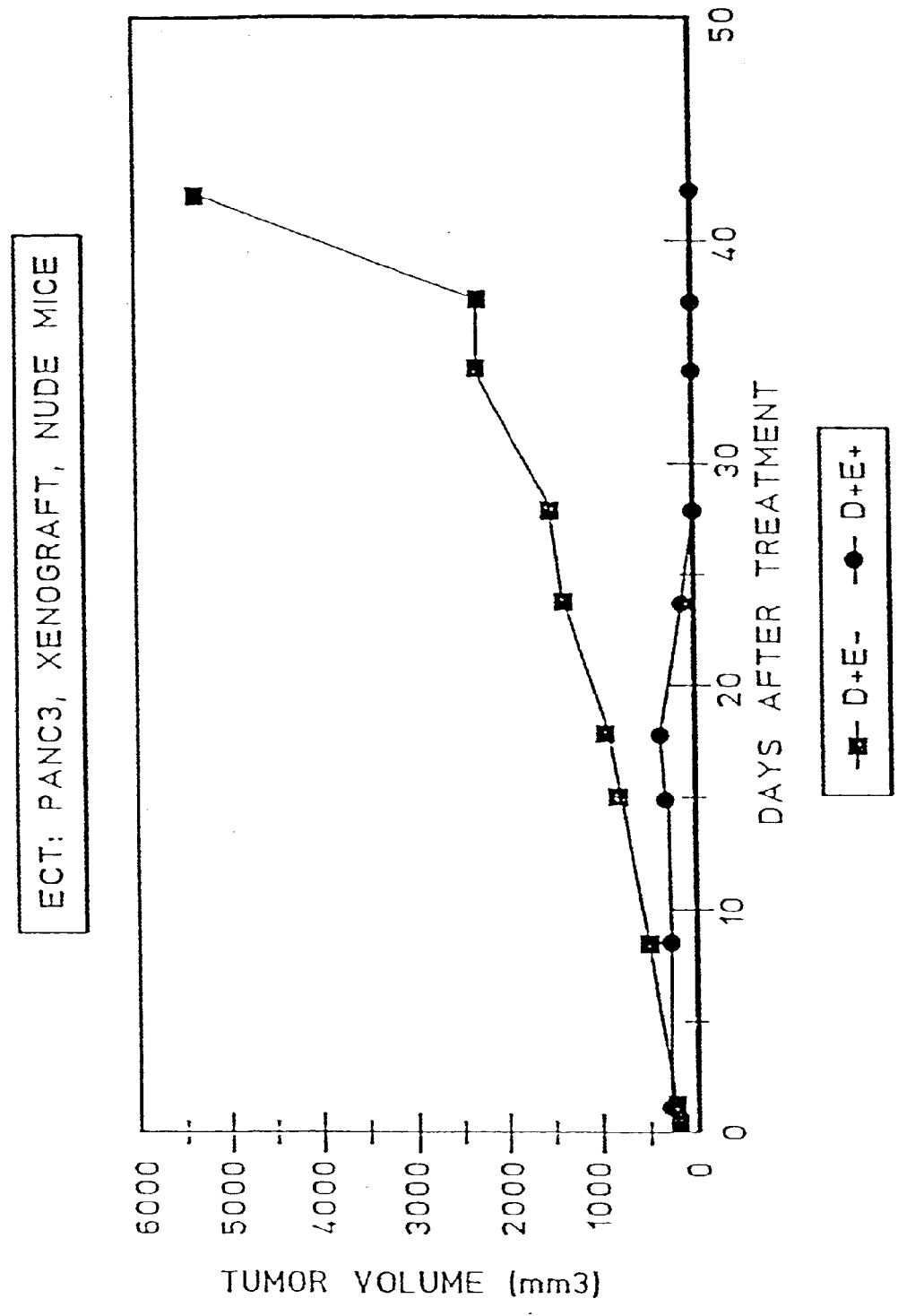
FIGS. 10a and 10b show the tumor volume after 43 days of ECT with bleomycin in Panc-3 xenografted nude mice. (D=drug; E=electroporation)
Figure 10B:
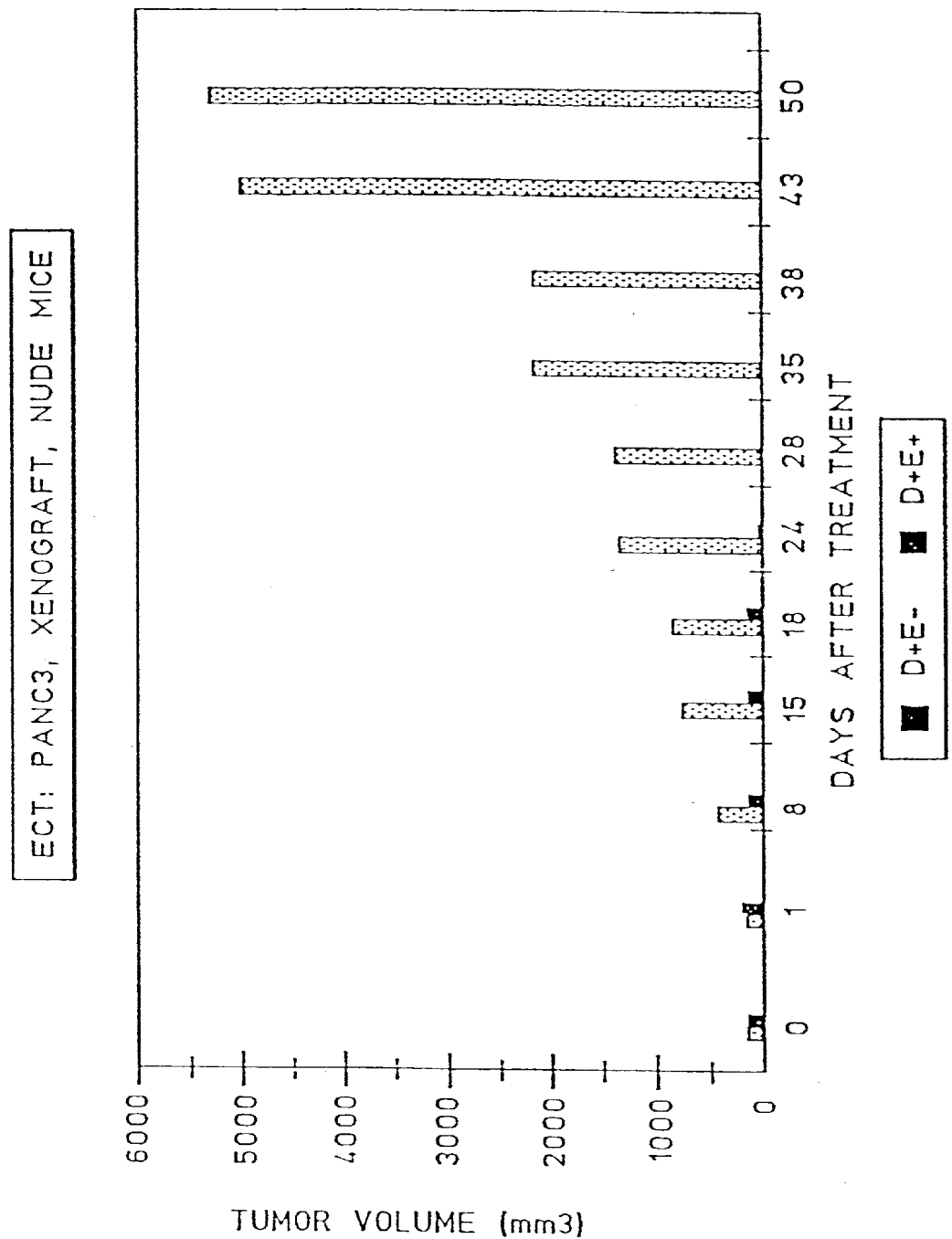

FIGS. 10a and 10b show the analysis of the tumor volume determined over a 43 day period after ECT using bleomycin for the Panc-3 tumors. There was a dramatic difference between the untreated and treated mice in terms of tumor volume. There was essentially no detectable tumor after approximately 24 days of treatment. The results of FIG. 10 are also summarized in Table 1 below. An illustration of the actual regression of the tumor is shown in FIG. 11.

TABLE 1

ELECTROCHEMOTHERAPY OF PANC-3 TUMORS IN NUDE MICE

| Days after treatment | Tumor volume (mm³) C1 | Tumor volume (mm³) C2 | Tumor volume (mm³) T1 | Tumor volume (mm³) T2 |
|---|---|---|---|---|
| 0 | 138.746 | 148.94 | 123.11 | 178.37 |
| 1 | 206.979 | 179.82 | 210.95 | 252.72 |
| 8 | 394.786 | 451.787 | 104.55 | 211.11 |
| 15 | 557.349 | 798.919 | 113.21 | 226.966 |
| 18 | 939.582 | 881.752 | 161.73 | 246.91 |
| 24 | 1391.057 | 1406.98 | 41.56 | 47.2228 |
| 28 | 1628.631 | 1474.21 | 0 | 0 |
| 35 | 2619.765 | 2330.31 | 0 | 0 |
| 38 | 2908.912 | 2333.967 | 0 | 0 |
| 43 | 3708.571 | 5381.759 | 0 | 0 |

Cell Line: poorly differentiated human pancreatic tumor (panc3)
Mouse model: nude mouse
Transplant: subcutaneous xenograft
Control mice: C1 and C2
Treated mice: T1 and T2

Figure 12A:
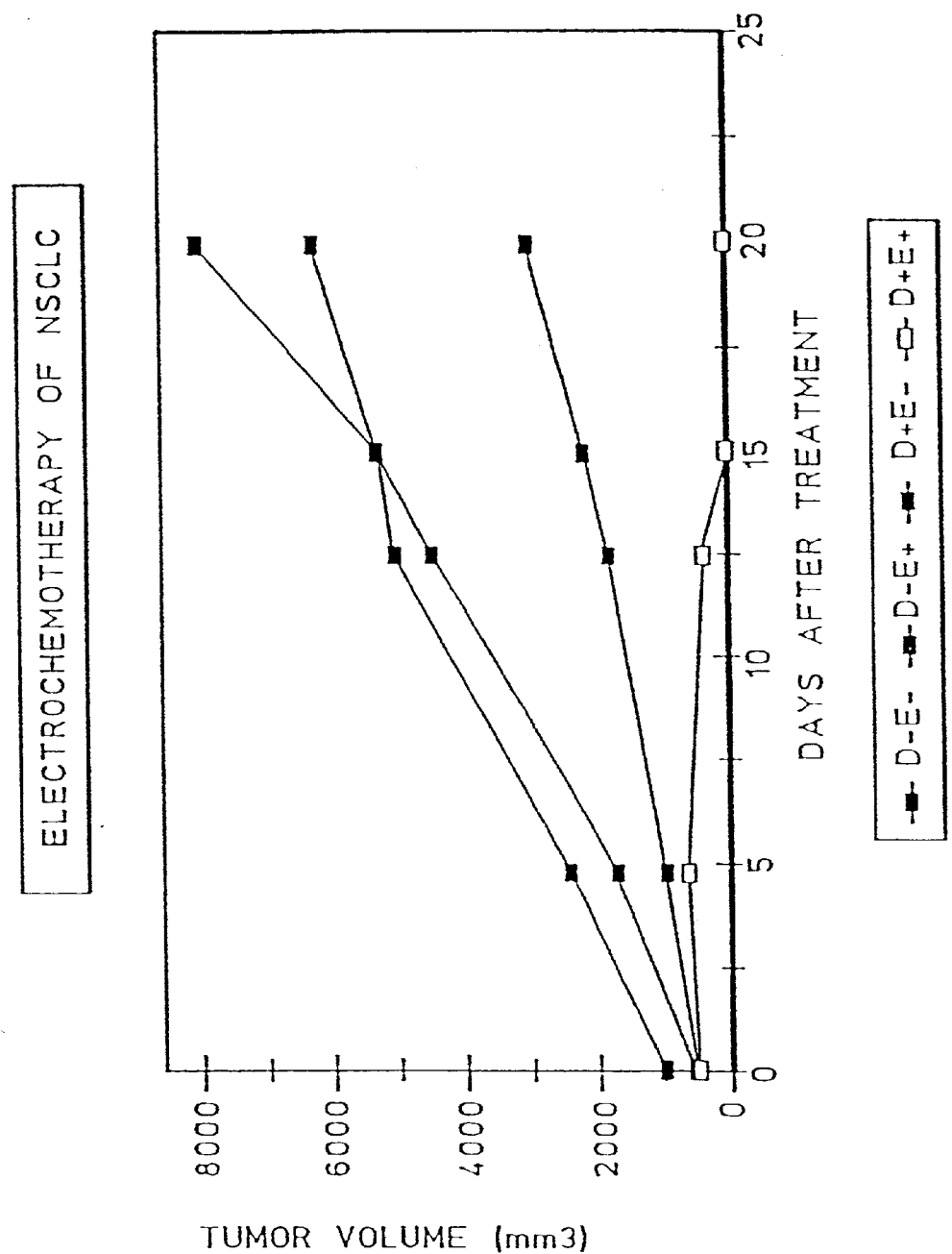
FIGS. 12a and 12b show the tumor volume after 20 and 34 days of ECT with bleomycin, respectively, in non-small cell lung carcinoma (NSCLC) xenografted nude mice. (D=drug; E=electroporation)
Figure 12B:
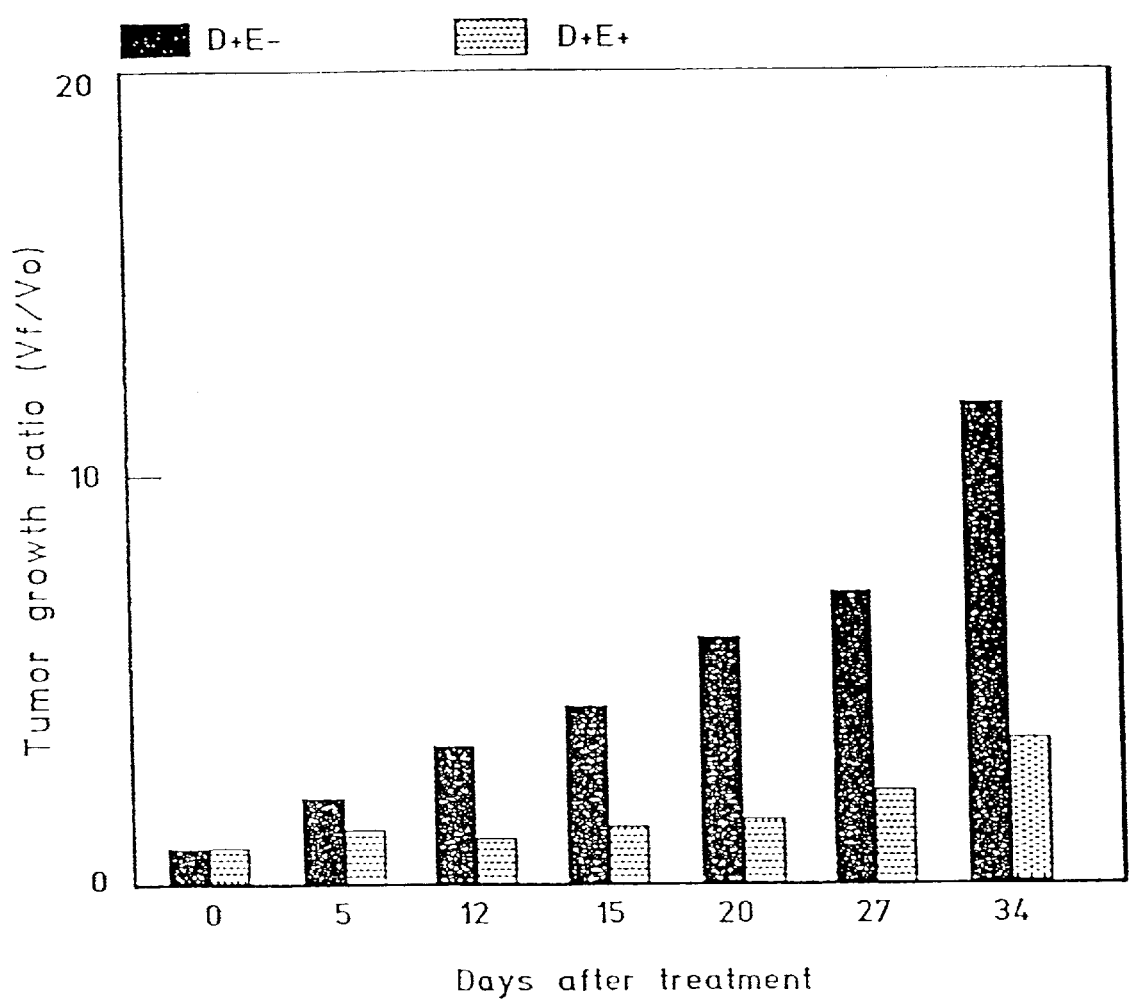
Figure 13:
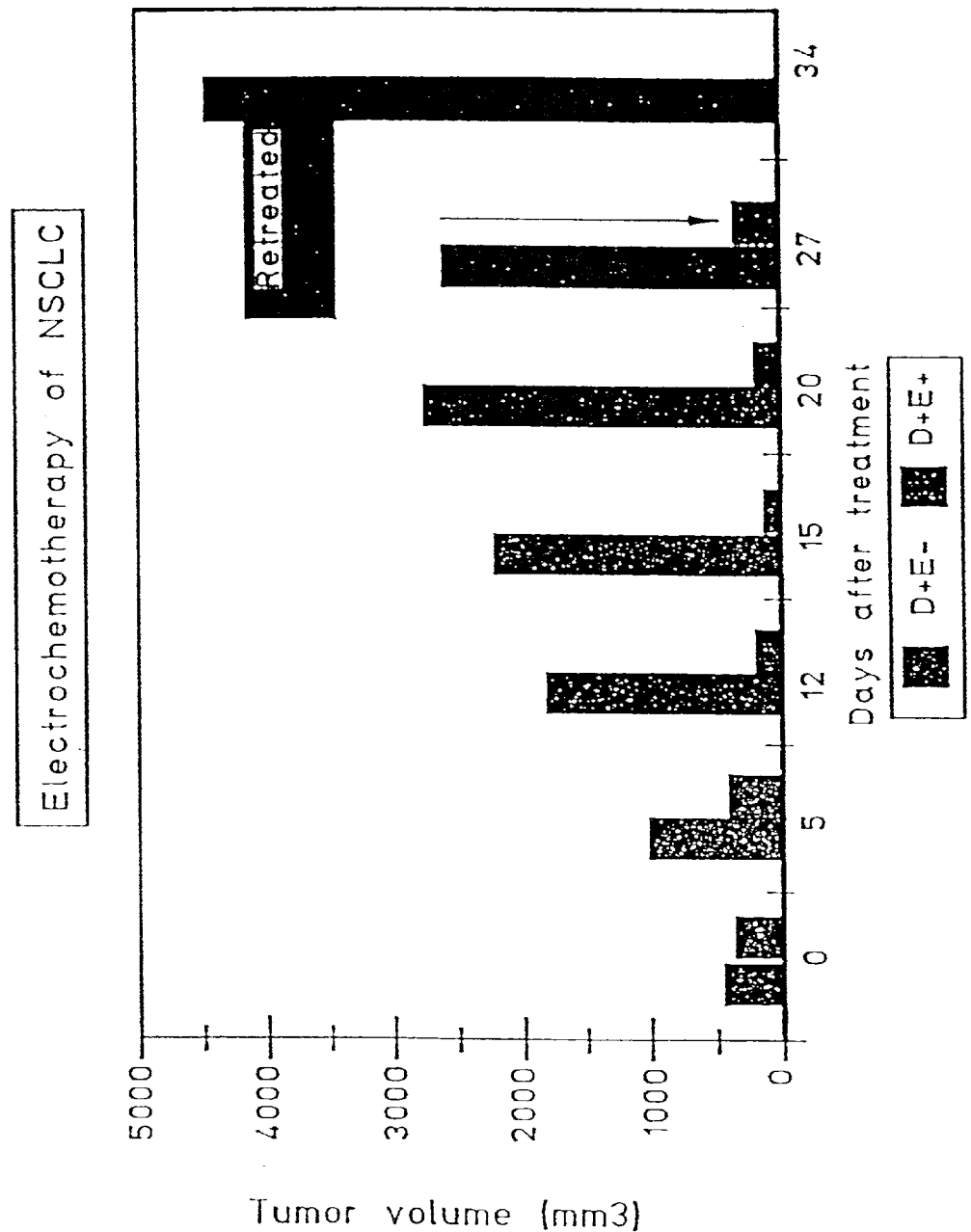
FIG. 13 shows the tumor volume after 34 days of ECT with bleomycin in non-small cell lung carcinoma (NSCLC) xenografted nude mice. The arrow indicates retreatment of one mouse at day 27. (D=drug; E=electroporation)

The Panc-3 experiment was repeated using a non-small cell lung cancer cell line (NSCLC), 177 (Anticancer, San Diego, Calif.). The results were similar to that found with bleomycin and Panc-3 as shown in FIGS. 12a and 12b. In one experiment, a tumor that had recurred was retreated at day 27 (FIG. 13) and after 7 days, there was no evidence of tumor.

Figure 14A:
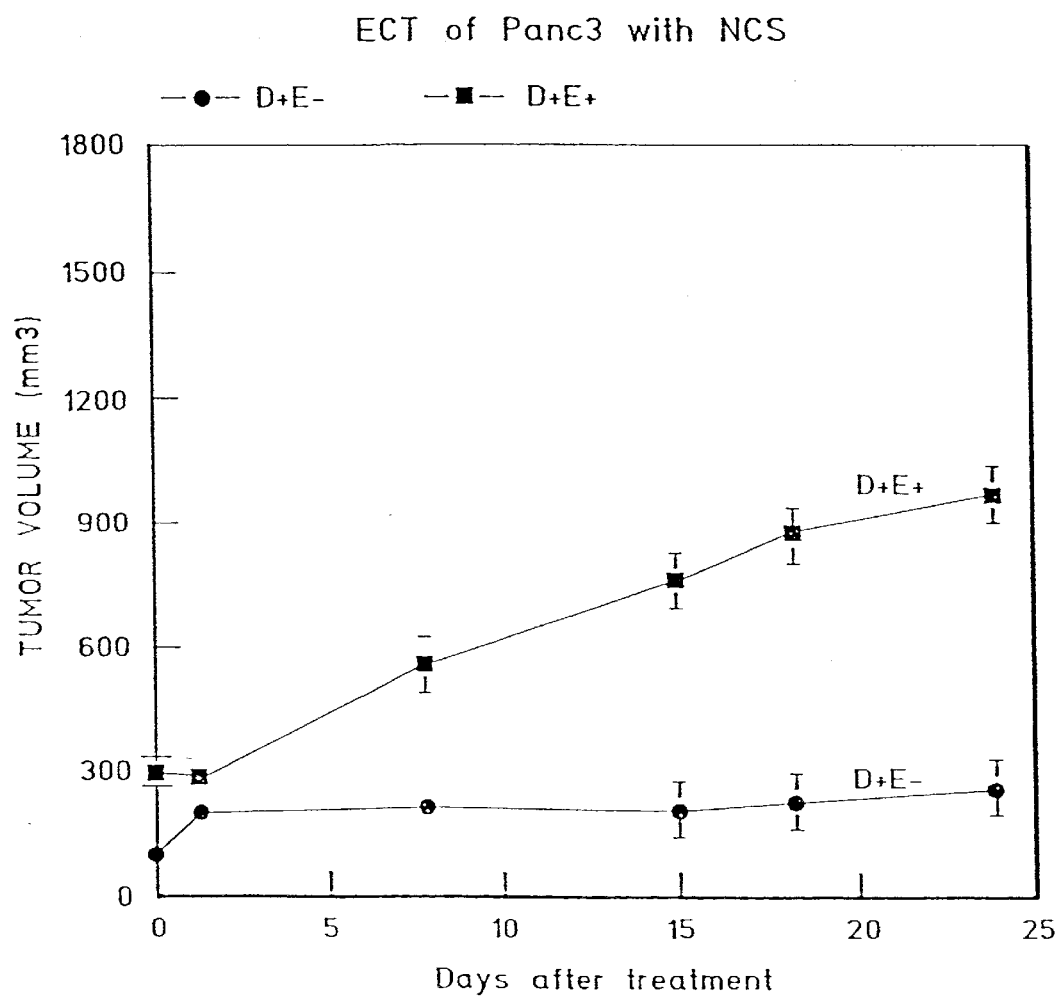
FIGS. 14a and 14b show pre-pulse dosing with neocarcinostatin in Panc-3 and NSCLC, respectively, in the nude mouse model.
Figure 14B:
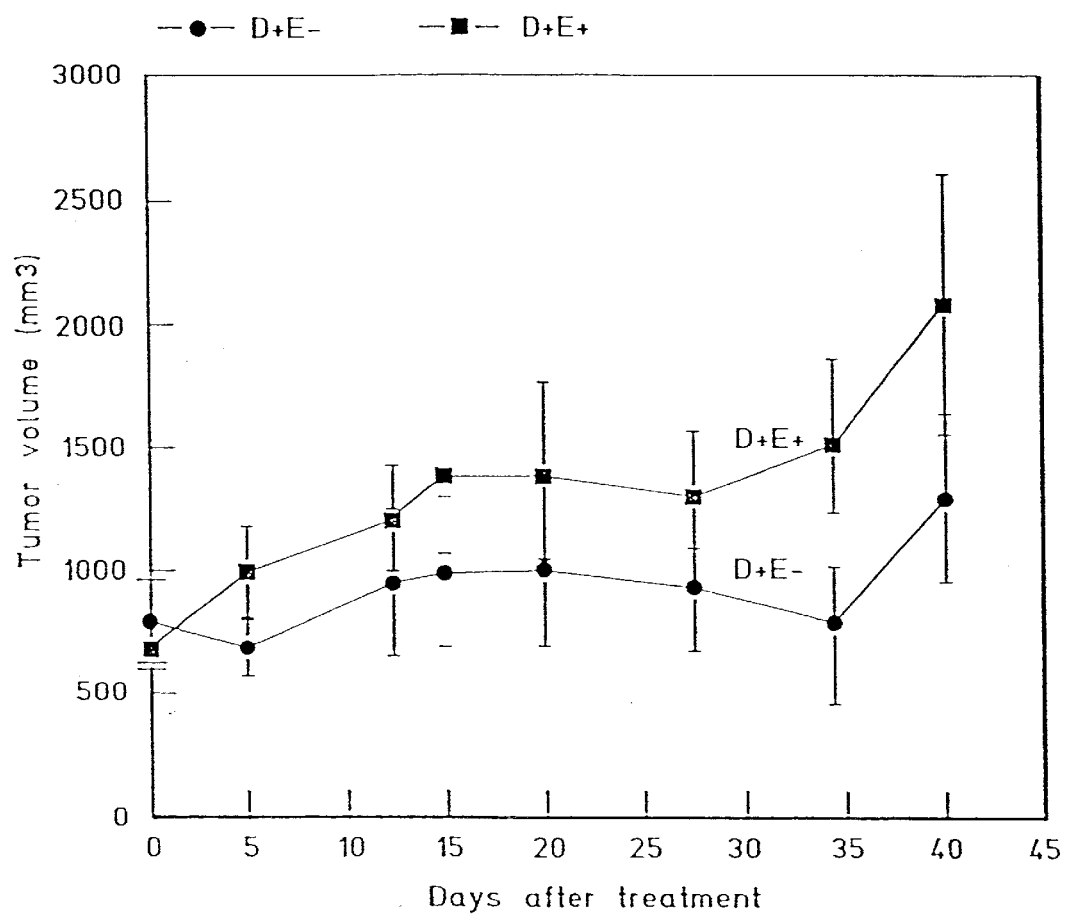

The Panc-3 and NSCLC models were utilized with the drug neocarcinostatin (NCS) following the same procedures as outlined above. As shown in FIGS. 14a and 14b, pre-pulse dosing with NCS in a manner similar to that used for the bleomycin studies, was not effective in reducing tumor size at all. It was believed that due to the low isoelectric point of NCS, electrostatic interaction prevented the drug from entering the tumor cell. Therefore, the experiment was repeated by pulsing first and injecting NCS post-pulse.

Figure 14C:
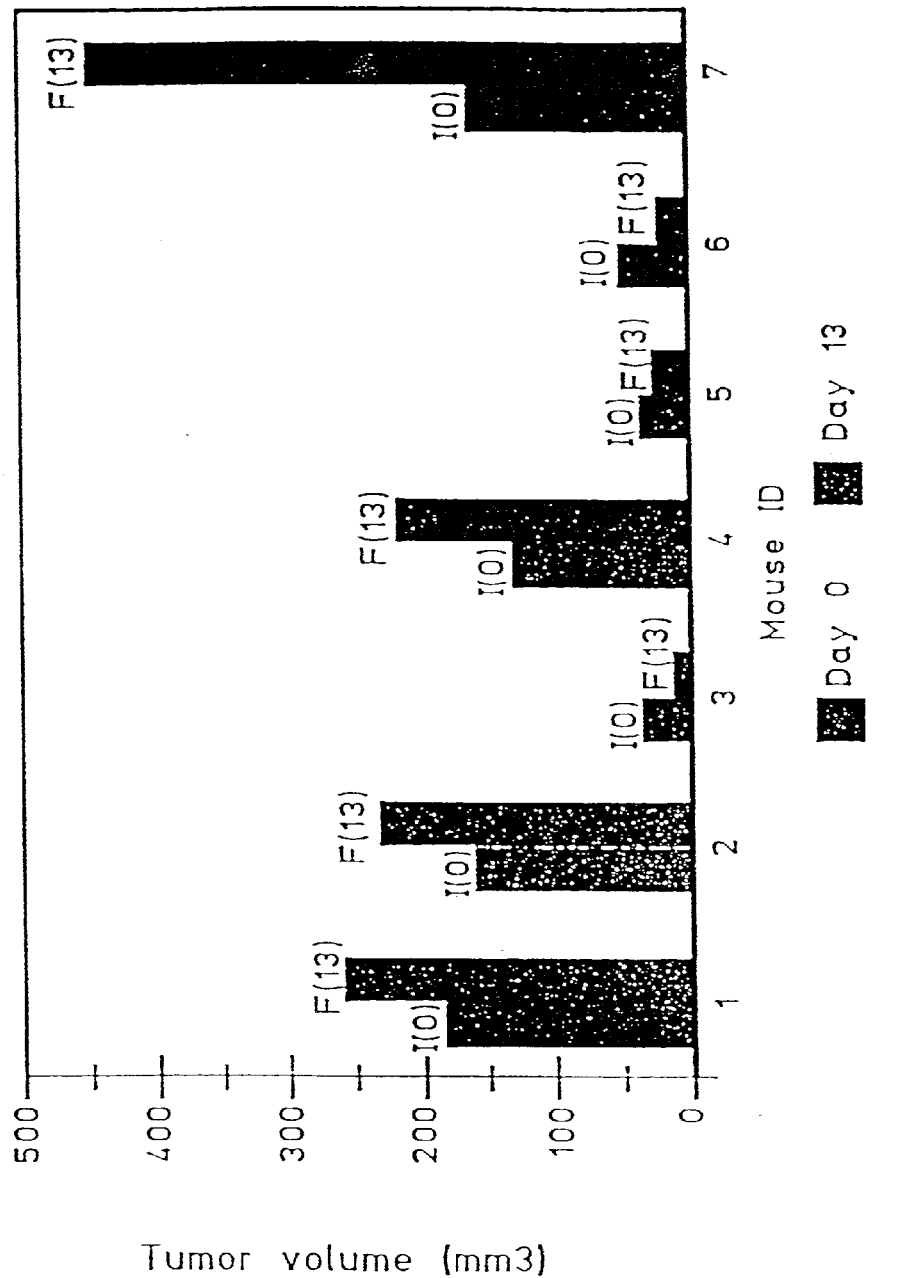
FIGS. 14c and 14d show post-pulse dosing with neocarcinostatin in Panc-3 in the nude mouse model.
Figure 14D:

FIG. 14c shows the initial tumor volume (I) as compared to the final tumor volume (F) at day 13 for 7 mice treated (Mouse ID 1–7). In several of the mice (ID 1, 2, 4, and 7), an increase in tumor volume was observed, but appeared to be due to edema. However, as shown in FIG. 14d, when a separate group of 5 mice were examined at day 23, all mice showed a marked reduction in tumor volume.

A comparison of FIGS. 14a and b with 14c and d indicated that post-pulse with NCS was more effective than pre-pulse administration for NCS.

SUMMARY

The present Examples illustrate that a poorly differentiated Pancreatic cancer (Panc-3) and Non-small cell lung cancer (NSCLC) xenografted subcutaneously onto nude mice can be effectively treated by the electrochemotherapy protocol using bleomycin or NCS and needle array electrodes. Other similar chemotherapeutic agents can also be effective using the method of the invention.

The results show a complete regression of Panc-3 tumors was achieved in 60% of the treated group with no palpable tumor seen even 77 days after the single treatment. Partial regression (80% reduction in tumor volume) was observed in 30% of cases, while only 10% did not respond (Table 2).

Histological studies clearly showed severe necrosis of the tumor region for the group subjected to ECT whereas no necrosis was apparent in the control group. Intratumoral drug injection with larger volume of bleomycin, combined with fanning to maximize uniform drug distribution throughout the tumor volume, was found to be very effective as compared to the conventional mode of injecting the drug prior to pulsing.

TABLE 2

Electrochemotherapy of Panc-3 with Bleomycin

| | Days after treatment | | | |
|---|---|---|---|---|
| | 28 | 35 | 57 | 77 |
| CR (100%) | 6 | 6 | 6 | 6 |
| PR (80%) | 3 | | | |
| NR (%) | 1 | 1 | 1 | 1 |
| Death | | | | 2* |
| Tumor regrowth | | 2 | | |
| Retreatment | | | 2 | |
| Histology | | 1 | | |

Number of mice treated: 10
CR: Complete Regression
PR: Partial Regression
NR: No Response
*1 mice died after retreatment
1 mice died after 64 days survival Although the invention has been described with reference to the presently preferred embodiment, it should be understood that various modifications can be made without departing from the spirit of the invention. Accordingly, the invention is limited only by the following claims.

What is claimed is:

1. A method for in vivo delivery of a recombinant expression vector into cells of a tissue of a patient, comprising:
    infusing the recombinant expression vector into a location selected for in vivo delivery of the recombinant expression vector within the tissue;
    inserting spaced electrodes into the selected location in the tissue;
    sensing the distance between said inserted electrodes and adjusting the voltage of a pulse generator proportionate to the sensed distance between the electrodes to achieve a desired electric field; and
    applying an electric signal to the electrodes to generate an electric field of a predetermined amplitude and duration in the tissue, thereby delivering the recombinant expression vector into the cells.

2. The method of claim 1, wherein the spaced electrodes are two electrodes.

3. The method of claim 1, wherein the spaced electrodes are electrodes in an array.

4. The method of claim 3, wherein the electrodes in the array are conductive needle electrodes.

5. The method of claim 1, wherein the recombinant expression vector is infused into the tissue using a syringe.

6. The method of claim 1, wherein the a recombinant expression vector encodes a therapeutic molecule selected from the group consisting of an anti-sense nucleic acid, a ribozyme, and a gene encoding a polypeptide.

7. The method of claim 1, used to treat disease.

8. The method of claim 1, wherein the electric signal applied to the electrodes has a voltage of at least about 0.2 kV per cm distance between the electrodes.

9. The method of claim 1, wherein the pulse length is at least about 10 microseconds.

10. The method of claim 1, wherein there are less than about 100 pulses per second.

11. The method of claim 1, wherein a waveform of the electrical signal is selected from the group consisting of an exponentially decaying pulse, a square pulse, a unipolar oscillating pulse train; and a bipolar oscillating pulse train.

12. A method for in vivo delivery of a pharmaceutical agent into cells of a tissue in a patient, comprising:
    infusing the pharmacological agent into a location within the tissue selected for in vivo delivery of the pharmacological agent;
    inserting spaced electrodes into the selected location in the tissue;
    sensing the distance between said inserted electrodes and adjusting the voltage of a pulse generator proportionate to the sensed distance between the electrodes to achieve a desired electric field; and
    applying an electric signal to the electrodes to generate an electric field of a predetermined amplitude and duration in the tissue, thereby delivering the recombinant expression vector into the cells.

13. The method of claim 12, wherein the spaced electrodes are two electrodes.

14. The method of claim 12, wherein the spaced electrodes are electrodes in an array.

15. The method of claim 14, wherein the electrodes in the array are conductive needle electrodes.

16. The method of claim 12, wherein the pharmacological agent is infused into the tissue using a syringe.

17. The method of claim 12, wherein the pharmacological agent is a recombinant expression vector encoding a molecule selected from the group consisting of an anti-sense nucleic acid, a ribozyme, and a gene encoding a polypeptide.

18. The method of claim 12, wherein the pharmacological agent is an antibody.

19. The method of claim 12, wherein the pharmacological agent is an anticancer drug.

20. The method of claim 12, wherein the method is used to treat disease.

21. The method of claim 12, wherein the electric signal applied to the electrodes has a voltage of at least about 0.2 kV per cm distance between electrodes.

22. The method of claim 12, wherein the pulse length is at least about 10 microseconds.

23. The method of claim 12, wherein there are less than about 100 pulses per second.

24. The method of claim 12, wherein a waveform of the electrical signal is selected from the group consisting of an exponentially decaying pulse, a square pulse, a unipolar oscillating pulse train, and a bipolar oscillating pulse train.

25. A method for therapeutic application of electroporation to a portion of a body of a patient for introducing a macromolecule into cells therein, comprising:
    providing an electric field generator comprising spaced electrodes for generating a desired electric field at a selected location within the patient's body;
    sensing the distance between said electrodes after insertion of said electrodes into the patient's body and adjusting the voltage of a pulse generator proportionate to the sensed distance between the electrodes to achieve a desired electric field;
    infusing the macromolecules into a selected location; and
    applying an electric signal from said pulse generator to the electrodes for causing said electrodes to generate the desired electric field with a predetermined amplitude and duration in the selected location within the body, thereby forcing the walls of cells in the selected location to be transiently permeable for permitting the macromolecule to enter the cells.

26. The method of claim 25, wherein the spaced electrodes are two electrodes.

27. The method of claim 25, wherein the spaced electrodes are electrodes in an array.

28. The method of claim 25, wherein the electrodes in the array are conductive needle electrodes.

29. The method of claim 25, wherein the macromolecule is infused into the tissue using a syringe.

30. The method of claim 25, wherein the macromolecule is a recombinant expression vector encoding a therapeutic molecule selected from the group consisting of an anti-sense nucleic acid, a ribozyme, and a gene encoding a polypeptide.

31. The method of claim 25, wherein the macromolecule is an antibody.

32. The method of claim 25, wherein the macromolecule is a pharmacological agent.

33. The method of claim 25, wherein the macromolecule is an anticancer drug.

34. The method of claim 25, wherein the macromolecule is a protein.

35. The method of claim 25, wherein the method is used to treat disease.

36. The method of claim 25, wherein the electric signal applied to the electrodes has a voltage of at least about 0.2 kV per cm distance between electrodes.

37. The method of claim 25, wherein the pulse length is at least about 10 microseconds.

38. The method of claim 25, wherein there are less than about 100 pulses per second.

39. The method of claim 25, wherein a waveform of the electrical signal is selected from the group consisting of an exponentially decaying pulse, a square pulse, a unipolar oscillating pulse train, and a bipolar oscillating pulse train.

* * * * *